United States Patent [19]

Hofbauer et al.

[11] 4,194,387
[45] Mar. 25, 1980

[54] TESTING APPARATUS

[75] Inventors: Rupert Hofbauer; Josef Svoboda, both of Schwechat, Austria

[73] Assignee: TMC Corporation, Baar, Switzerland

[21] Appl. No.: 928,167

[22] Filed: Jul. 26, 1978

[30] Foreign Application Priority Data

Aug. 16, 1977 [AT] Austria .............................. 5902/77

[51] Int. Cl.² ............................................. G01N 19/02
[52] U.S. Cl. ....................................................... 73/9
[58] Field of Search .......................... 73/9, 7, 432 SD; 12/14.4

[56] References Cited

U.S. PATENT DOCUMENTS

| | | | |
|---|---|---|---|
| 358,164 | 2/1887 | Post | 73/9 |
| 974,202 | 11/1910 | Stiggins | 12/14.4 |
| 1,030,821 | 6/1912 | Keith | 12/14.4 |
| 2,225,140 | 12/1940 | Walker | 73/9 |
| 2,944,417 | 7/1960 | Stupp | 73/9 |

*Primary Examiner*—S. Clement Swisher
*Assistant Examiner*—Denis E. Corr
*Attorney, Agent, or Firm*—Blanchard, Flynn, Thiel, Boutell & Tanis

[57] ABSTRACT

A testing apparatus for testing the sliding characteristics of the soles of ski boots. The testing apparatus includes a lever arm for applying a downwardly directed force onto an upwardly facing boot sole adjacent structure engaging either the toe or heel of the ski boot. A drive mechanism is utilized to draw the member which is applying the downwardly directed force laterally of the ski boot. A measuring device is provided for detecting the sliding characteristic of the member which applies the downwardly directed force onto the upwardly facing boot sole.

6 Claims, 2 Drawing Figures

TESTING APPARATUS

FIELD OF THE INVENTION

The invention relates to a testing apparatus for determining the sliding characteristics of ski boot soles.

BACKGROUND OF THE INVENTION

In known apparatus of this kind, the ski boot which was to be tested was placed on the testing apparatus with a downwardly facing sole, and the upper part of the boot was removed at least in the area of the toe of the boot in order to achieve exact load forces. As a result thereof, the boots which were exposed to a measurement procedure were automatically destroyed.

An object of the present invention is to provide a device for determining the characteristics of the boot sole in the connecting and sliding area so that both the size and also the type of shoe to be tested can be changed and also the loads can be varied in accordance with a relationship to the sliding characteristics which must be measured, without requiring a destruction of the boots which must be tested.

The foregoing object as well as other objects are inventively attained by the provision of a load mechanism for applying a load force to a part of the sole of the boot which is to be tested, particularly by the interpositioning of a slide piece. The load force can be varied at differently high load forces. The load mechanism applies a load force, which is at least approximately vertical, onto the sliding piece. A measuring device for measuring and/or registering of the force is provided as well as a fastening device for holding the ski boot in place. The fastening device has a boot-receiving mounting which includes a cleat so that the boot to be tested can be mounted on the boot-receiving mounting with the sole facing upwardly. The sole is inserted between two parts of the fastening device, which parts can be adjusted both in elevational and also in longitudinal direction and can be secured in same and the cleat receiving the boot is, as is known, adjustable in longitudinal direction of the boot.

The inventive measure permits a carrying out of exact comparable and, if necessary, repeatable measurements in a simple manner without destroying the boot material and the test results which are obtained are if needed also registered.

A particularly advantageous embodiment of the invention includes a device which applies onto the slide piece a force which is approximately perpendicular to the load force, which device is an electric motor. The electric motor is coupled to the slide piece for example by means of a cable. In this manner, the magnitude of the load forces which must be applied onto the slide piece can easily be regulated and also their direction can be adjusted or maintained.

In a further development of the thought of the invention, several selectively applicable slide pieces are provided which are constructed with different coatings and/or structure and preferably have the same cross sections. This measure assures a standardization of the boot-sole characteristics since the comparison values can be kept equal with one another under all circumstances.

In order to obtain comparable test results, it is further inventively provided that the cross section of the slide pieces which are used is at least as large, preferably larger, than the area of the boot, which is to be tested.

BRIEF DESCRIPTION OF THE DRAWING

Further advantages and details of the invention are discussed more in detail with reference to the drawing, which illustrates one exemplary embodiment.

In the drawing.

DETAILED DESCRIPTION

Figure 1:
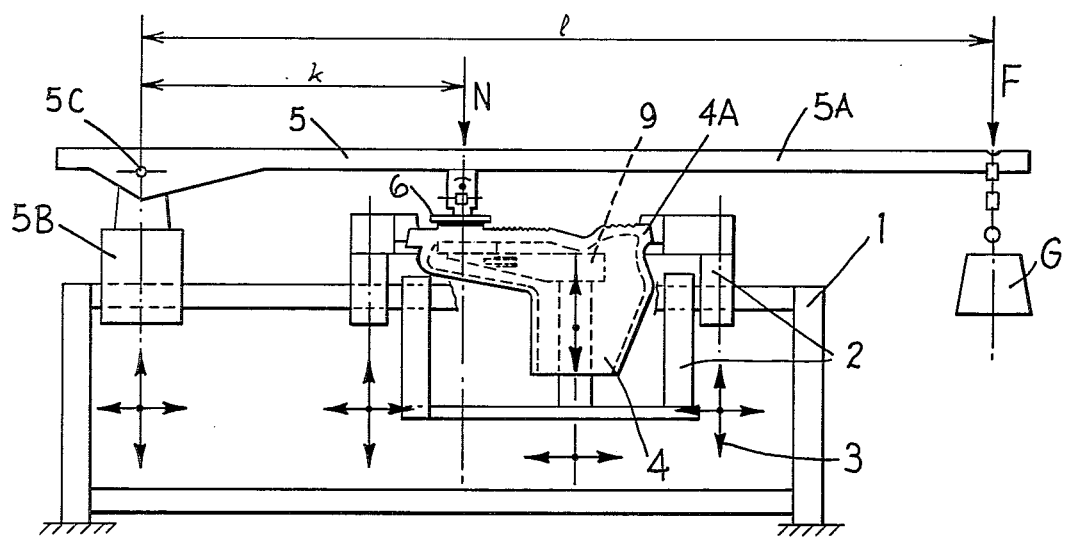
FIG. 1 is a front view of the inventive testing apparatus.
Figure 2:
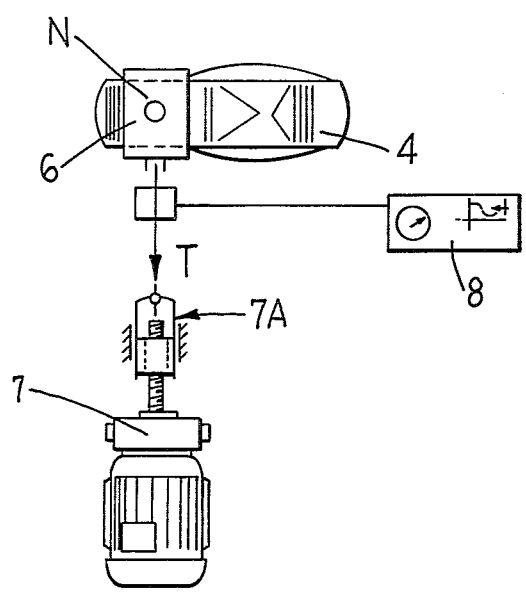
FIG. 2 is a top view of a portion of FIG. 1.

Parts of a fastening device 2 are arranged on a frame 1. These parts of the fastening device 2 can be adjusted along rods on the frame 1 in direction of the arrow 3 (left, right, up and down) and can be secured in the desired position in a conventional manner, for example by means of locking screws. A boot-receiving mounting 9 is provided on a part of the fastening device 2, which mounting is constructed like a cleat, however, having a sufficiently large place to receive differently sized boots. The toe engaging part of the cleat can be adjusted in relationship to the heel engaging part, for example by using a rotatably supported threaded rod and an internally threaded sleeve nut which is in threaded engagement with the threaded rod. These parts, however, are not the subject matter of the present invention and are not shown in the drawing. A boot shell 4 is mounted on the boot-receiving mounting 9, which shell, as can be recognized particularly from FIG. 1, has an upwardly facing sole 4a, the inside surface thereof resting on the boot-receiving mounting 9. The boot sole 4a is held between the parts of the fastening device 2. Since the boot sole 4a is supported from the inside on the boot-receiving mounting 9, the force identified by the arrow N, is applied by a load mechanism 5 which includes a variable weight G. The load mechanism 5 includes a lever arm 5A pivotally secured to a block 5B mounted on the frame 1. A slide piece 6 is secured to the lever arm 5A intermediate the length thereof. A weight G is suspended from the end of a chain secured to the end of the lever arm remote from the block 5B. The length of the lever arm between the pivot axis 5C and the point of application of the weight G to generate a force vector F is "$l$". The spacing between the pivot axis 5C and the slide piece 6 is "$k$". The variable weight G can easily be calculated due to the formula $l \times F = k \times N$.

The slide piece 6 is arranged centrally with respect to the point of application the force which is identified by the arrow N, which slide piece is pulled in direction of the arrow T by a cable secured to a pulling device 7A responsive to the rotary output of an electric motor 7, which cable is not identified in detail. The measuring device 8 is operatively connected to the cable. The force T which is hereby produced and which is directed at least perpendicular to the load force N which is applied on the slide piece 6 is measured by means of a measuring device 8. The measured values obtained from this test permit one to draw conclusions with respect to the sliding characteristics of the boot sole in relationship to the characteristics of the boot sole, temperature, wetness, dirt, etc. The obtained measured values of different products can be compared with one another and can be evaluated on a common base. If desired, several sliding pieces can be provided, each of which has a different sliding characteristic. The differing sliding pieces can have differing materials thereon to achieve the different sliding characteristics.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A testing apparatus for determining the sliding characteristics of a ski boot sole, comprising:
   a frame;
   fastening means for fastening a ski boot to said frame;
   a sliding piece means for engaging a part of said boot sole to be tested;
   first load applying means mounted on said frame for applying a first load force to said sliding piece and in a first direction perpendicular to the surface of said boot sole;
   second load applying means mounted on said frame for applying a second load force to said sliding piece and in a second direction parallel to said surface of said boot sole, said second load applying means including an electric motor having a rotary output and first means for converting said rotary output to a linear movement, said sliding piece means being operatively secured to a linearly movable part of said first means; and
   measuring means for measuring the magnitude of said second load force.

2. The testing apparatus according to claim 1, wherein several, selectively applicable sliding pieces are provided, each of which is constructed with differing sliding materials and differing sliding characteristics and equal cross sections.

3. The testing apparatus according to claim 1, wherein the cross section of said sliding piece is at least as large as the area of said ski boot sole which is to be tested.

4. The testing apparatus according to claim 1, wherein said fastening means includes a boot-receiving mounting member for receiving a ski boot thereon with said sole thereof facing upwardly and toe and heel engaging means for holding the toe and heel portions of said ski boot sole in a fixed position.

5. The testing apparatus according to claim 1, wherein several, selectively applicable sliding pieces are provided, each of which is constructed with differing sliding characteristics and equal cross sections.

6. The testing apparatus according to claim 1, wherein several, selectively applicable sliding pieces are provided, each of which is constructed with differing sliding materials and equal cross sections.

* * * * *